United States Patent
Leeb

(10) Patent No.: US 9,157,114 B2
(45) Date of Patent: Oct. 13, 2015

(54) METHOD OF DETERMINING THE GENOTYPE RELATING TO HEREDITARY NASAL PARAKERATOSIS (HNPK) AND NUCLEIC ACIDS USABLE IN SAID METHOD

(71) Applicant: University of Bern, Bern (CH)

(72) Inventor: Tosso Leeb, Wabern (CH)

(73) Assignee: UNIVERSITY OF BERN, Bern (CH)

( * ) Notice: Subject to any disclaimer, the term of this patent is extended or adjusted under 35 U.S.C. 154(b) by 55 days.

(21) Appl. No.: 13/899,122

(22) Filed: May 21, 2013

(65) Prior Publication Data

US 2013/0316345 A1    Nov. 28, 2013

(30) Foreign Application Priority Data

May 25, 2012  (FI) .................................. 2012/5554

(51) Int. Cl.
*C07H 21/04* (2006.01)
*C12Q 1/68* (2006.01)

(52) U.S. Cl.
CPC ............ *C12Q 1/6827* (2013.01); *C12Q 1/6883* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 7,052,889 B2 | 5/2006 | Jenuwein et al. | |
| 2002/0039776 A1 | 4/2002 | Jenuwein et al. | |
| 2003/0092019 A1* | 5/2003 | Meyer et al. ....................... | 435/6 |

FOREIGN PATENT DOCUMENTS

WO    2012164936 A1    12/2012

OTHER PUBLICATIONS

Lucentini (The Scientist; 2004, vol. 24, p. 20).*
Ioannidis (Nature Genetics, vol. 29, pp. 306-309, Nov. 2001).*
Tacher et al. (J. of Heredity, vol. 96, No. 7, pp. 812-816, 2005).*
Jagannathan et al. (PLOS Genetics, vol. 9, No. 10, e1003848, Oct. 3, 2013).*
Lindblad-Toh et al. (Broad Institute, Nature, vol. 438, pp. 803-819, Dec. 2005).*
European Patent Office, Extended European Search Report, EP 13167812, Aug. 13, 2013, 8 pages.
Lachaume, et al., Identification and Analysis of the Dog Keratin 9 (KRT9) Gene, Animal Genetics, 1998, 29:173-177.
Database UniProt [Online], Subname: Full=Uncharacterized protein, XP002708066, Nov. 30, 2010, 1 page.
Page, N. et al., "Case Report Hereditary nasal parakeratosis in Labrador Retrievers", 2003, Veterinary Dermatology, vol. 14, pp. 103-110.
Peters, J. et al., "Hereditary nasal parakeratosis in Labrador retrievers: 11 new cases and a retrospective study on the presence of accumulations of serum ('serum lakes') in the epidermis of parakeratotic dermatoses and inflamed nasal plana of dogs", 2003, Veterinary Dermatology, vol. 14, pp. 197-206.
Purcell, S. et al., "PLINK: A tool set for whole-genome association and population-based linkage analyses", 2007, American Journal of Human Genetics, vol. 81, pp. 559-575.
Genebank Database (online), NCBI Reference Sequence: XM_535179.3, "Predicted: *Canis lupus familiaris* supressor of variegation 3-9 homolog (*Drosophila*), Transcript variatn 1 (SUV39 H2), mRNA", 2011.
Purcell, S. et al., "PLINK: Whole genome data analysis toolset", 2009, release v1.07, http://pngu.mgh.harvard.edu/~purcell/plink/.

* cited by examiner

*Primary Examiner* — Jeanine A Goldberg
(74) *Attorney, Agent, or Firm* — Quarles & Brady, LLP

(57) ABSTRACT

The invention concerns an in vitro method of determining a genotype relating to hereditary nasal parakeratosis (HNPK) in a dog. According to the invention the presence or the absence of a genetic variation in the SUV39H2 gene sequence is indicative of said disorder. The invention also concerns polypeptide based methods for determining said disorder. Further, nucleic acids, polypeptides and antibodies usable in said method are disclosed.

5 Claims, 6 Drawing Sheets

Fig. 2

A Top strand

CTGGATTATGAATCTGATGAATTCACAGTGGATGCAGCCCGATATGGAAA [T/G] GTCTCTCATTTTGTTAATCACAGTGTAAGTGATACTTAAAGAATAGACAG

SUV39H2 c.972T>G, p.N324K

T: wildtype

G: HNPK

B Forward strand

Genomic coordinate
on CFA 2
(CanFam 3 assembly)

```
21,731,342     1 tcctctatat gaagagaaaa ccttacaaag ttttgaaaag attagatgaa atacataaaa
21,731,402    61 tctcttgcaa aatgcctggt atttggtagt cacctcaatg aatttttctaa atacagcaat
21,731,462   121 aataccacaa cctaactgaa gagttctttg tattaaaatg ctttggaaaa aaaaaaaaaa
21,731,522   181 tgctttggaa ggacgcctgg gtgctcagcg gttgagcatc ttgccttccg ctcagggcat
21,731,582   241 gatcccagag ttccaggatc gaatcccaca tcgggctccc tgcatggagc ctgcttttcc
21,731,642   301 ctctgtctgt gtcactgcac ccccccccc catctctcat gaataaacaa aatcttaaaa
21,731,702   361 aaaatgcttt ggaaatatta aaagggtaag taacttaaat actcctcaac tatggacaaa
21,731,762   421 tcgttaaaaa cagtactaag ttgattagtc ctgtctattc tttaagtatc acttacactg
```

A>C causal mutation for nasal parakeratosis (HNPK)
                                   ↓

```
21,731,822   481 tgattaacaa aatgagagac atttccatat cgggctgcat ccactgtgaa ttcatcagat
```

T>C neutral polymorphism
                                                                ↓

```
21,731,882   541 tcataatcca gatcaaagag atatgtgatt cccttgttgt catataattg tccccgtctt
21,731,942   601 tcagcttctt cgcttgtgat tacctaaaaa gaagaaacta tagtatatta tatagctatt
21,732,002   661 gttgaattga acactcaccc ataaatctat tattaattta ttaatgcctt aacaacaaag
21,732,062   721 gtttagaaag taagaaattg aggtgtcttt aaaacaaata ttcagggatg cctgggtggt
21,732,122   781 tcagatggtt gggcatccac ctttggctca agtcatgatc tctagatcct gggatagagc
21,732,182   841 cccatgttgg ggtcccagct cagtgggag tctgcttctc cctctgtctc tcttcctgct
``` polymorphic microsatellite, many different alleles
                    ↓↓↓↓↓↓↓↓↓↓↓↓

```
21,732,242   901 tgtgcgcgct ctctctcttg ctttcaaatg aataaaaaaa atgttaaaaa aaataaaaca
21,732,302   961 tatttacaca agagctacaa gagctctcta caagagctga a
```

Genomic CFA 2: g.21,731,842A>C (CanFam 3.1 assembly, NCBI)

A: wildtype

C: HNPK

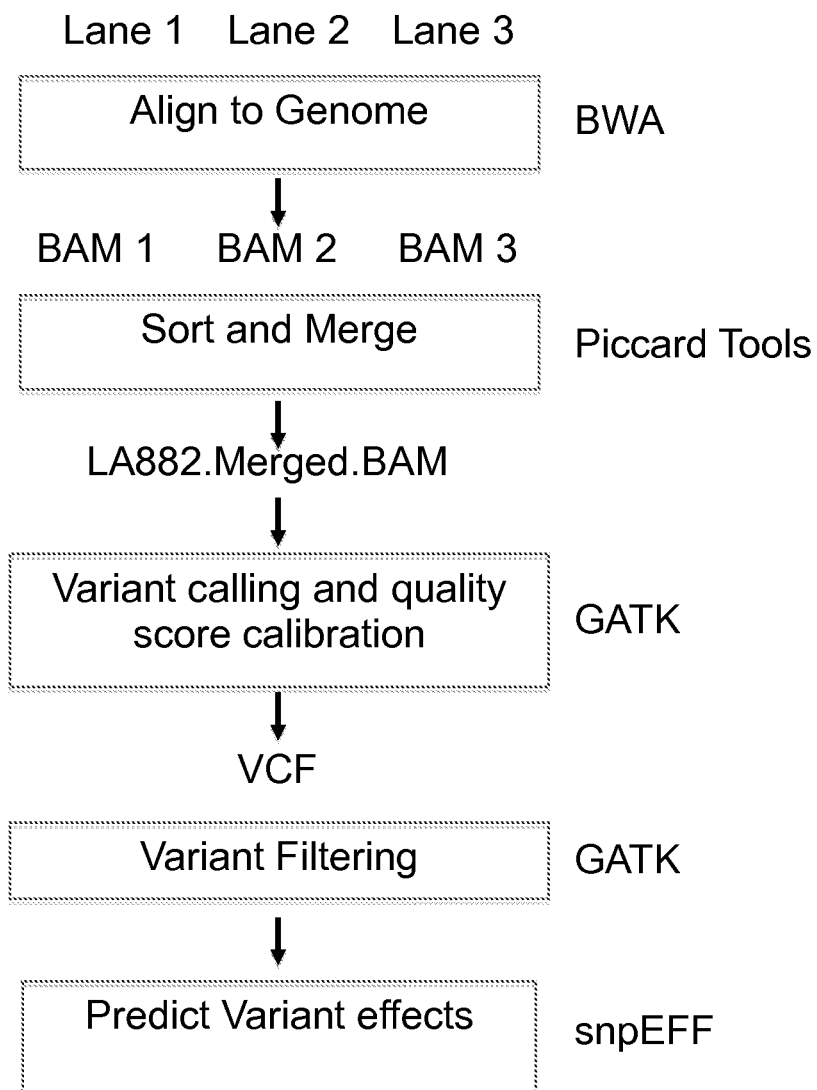

```
                           p.N324K
                             ↓
SUV39H2  dog      EFTVDAARYG  N  VSHFVNHSCD
         human    ..........  .  ..........
         cow      ..........  .  ..........
         mouse    ..........  .  ..........
         chicken  ..........  .  ..........
         frog     ..........  .  ..........

SUV39H1  human    VY.....Y..  .  I.........
EHMT1    human    VYCI..RF..  .  ..R.I..H.E
EHMT2    human    VYCI..RY..  .  I.R.I..L..
SETDB1   human    CYII..KLE.  .  LGRYL....S
SETDB2   human    V.LL..TKE.  .  .GR.L....C
```

Fig. 6

27 Positional Candidate Genes (HSA10 annotation, build 37.2)

| start | stop | Symbol | O | Description |
|---|---|---|---|---|
| 13'665'706 | 14'372'866 | FRMD4A | - | FERM domain containing 4A |
| 14'425'138 | 14'425'276 | MIR4293 | - | microRNA 4293 |
| 14'478'575 | 14'478'668 | MIR1265 | + | microRNA 1265 |
| 14'560'559 | 14'816'896 | FAM107B | - | family with sequence similarity 107, member B |
| 14'568'478 | 14'568'847 | LOC100507309 | - | hypothetical LOC100507309 |
| 14'687'198 | 14'608'832 | LOC100507281 | - | hypothetical protein LOC100507281 |
| 14'765'098 | 14'766'138 | RPSAP7 | - | ribosomal protein SA pseudogene 7 |
| 14'861'251 | 14'873'963 | CDNF | - | cerebral dopamine neurotrophic factor |
| 14'880'261 | 14'913'748 | HSPA14 | + | heat shock 70kDa protein 14 |
| 14'884'305 | 14'884'927 | LOC100421372 | + | zinc finger and SCAN domain containing 29 pseudogene |
| 14'920'782 | 14'946'314 | SUV39H2 | + | suppressor of variegation 3-9 homolog 2 (Drosophila) |
| 14'948'870 | 14'996'094 | DCLRE1C | - | DNA cross-link repair 1C |
| 15'001'438 | 15'014'858 | MEIG1 | + | meiosis expressed gene 1 homolog (mouse) |
| 15'026'675 | 15'029'478 | OR7E110P | - | olfactory receptor, family 7, subfamily E, member 110 pseudogene |
| 15'041'198 | 15'041'851 | OR7E26P | - | olfactory receptor, family 7, subfamily E, member 26 pseudogene |
| 15'049'787 | 15'050'726 | OR7E116P | - | olfactory receptor, family 7, subfamily E, member 116 pseudogene |
| 15'057'357 | 15'077'424 | LOC100289151 | - | hypothetical protein LOC100289151 |
| 15'085'895 | 15'115'851 | OLAH | + | oleoyl-ACP hydrolase |
| 15'117'474 | 15'130'778 | ACBD7 | - | acyl-CoA binding domain containing 7 |
| 15'135'060 | 15'135'612 | LOC100249710 | - | glyceraldehyde 3 phosphate dehydrogenase pseudogene 45 |
| 15'137'384 | 15'139'318 | C10orf111 | - | chromosome 10 open reading frame 111 |
| 15'139'182 | 15'146'256 | RPP38 | + | ribonuclease P/MRP 38kDa subunit |
| 15'147'771 | 15'218'695 | NMT2 | - | N-myristoyltransferase 2 |
| 15'196'721 | 15'197'346 | LOC100819204 | - | peptidylprolyl isomerase A pseudogene |
| 15'253'642 | 15'413'058 | FAM171A1 | - | family with sequence similarity 171, member A1 |
| 15'559'088 | 15'761'778 | ITGA8 | - | integrin, alpha 8 |
| 15'820'175 | 15'902'519 | FAM188A | - | family with sequence similarity 188, member A |

SEQUENCE LISTING

```
<160> NUMBER OF SEQ ID NOS: 6

<210> SEQ ID NO 1
<211> LENGTH: 410
<212> TYPE: PRT
<213> ORGANISM: Canis lupus familiaris

<400> SEQUENCE: 1

Met Ala Ala Ala Gly Ala Glu Ala Arg Arg Ala Trp Cys Val Pro Cys
1               5                   10                  15

Leu Val Ser Leu Asp Thr Leu Gln Glu Leu Cys Arg Lys Glu Lys Leu
            20                  25                  30

Thr Cys Lys Ser Ile Gly Ile Thr Lys Arg Asn Leu Asn Asn Tyr Glu
        35                  40                  45

Val Glu Tyr Leu Cys Asp Tyr Lys Val Val Lys Asp Met Glu Tyr Tyr
    50                  55                  60

Leu Val Lys Trp Lys Gly Trp Pro Asp Ser Thr Asn Thr Trp Glu Pro
65                  70                  75                  80

Leu Gln Asn Leu Lys Cys Pro Leu Leu Leu Gln Gln Phe Ser Asn Asp
                85                  90                  95

Lys His Asn Tyr Leu Ser Gln Val Lys Lys Gly Lys Ala Ile Ser Leu
            100                 105                 110

Lys Asp Asn Asn Lys Ala Leu Lys Pro Ala Ile Ala Glu Tyr Ile Val
        115                 120                 125

Lys Lys Ala Lys Gln Arg Ile Ala Leu Gln Arg Trp Gln Asp Glu Leu
    130                 135                 140
```

```
Asn Arg Arg Lys Asn His Lys Gly Met Ile Phe Val Glu Asn Thr Val
145                 150                 155                 160

Asp Leu Glu Gly Pro Pro Ser Asp Phe Tyr Tyr Ile Asn Glu Tyr Lys
                165                 170                 175

Pro Ala Pro Gly Ile Ser Leu Val Asn Glu Ala Thr Phe Gly Cys Ser
            180                 185                 190

Cys Thr Asp Cys Phe Phe Glu Lys Cys Cys Pro Ala Glu Ala Gly Val
        195                 200                 205

Leu Leu Ala Tyr Asn Lys Asn Gln Gln Ile Lys Ile Pro Pro Gly Thr
    210                 215                 220

Pro Ile Tyr Glu Cys Asn Ser Arg Cys Gln Cys Gly Pro Asp Cys Pro
225                 230                 235                 240

Asn Arg Ile Val Gln Lys Gly Thr Gln Tyr Ser Leu Cys Ile Phe Arg
                245                 250                 255

Thr Ser Asn Gly Cys Gly Trp Gly Val Lys Thr Leu Val Lys Ile Lys
            260                 265                 270

Arg Met Ser Phe Val Met Glu Tyr Val Gly Glu Val Ile Thr Ser Glu
        275                 280                 285

Glu Ala Glu Arg Arg Gly Gln Leu Tyr Asp Asn Lys Gly Ile Thr Tyr
    290                 295                 300

Leu Phe Asp Leu Asp Tyr Glu Ser Asp Glu Phe Thr Val Asp Ala Ala
305                 310                 315                 320

Arg Tyr Gly Asn Val Ser His Phe Val Asn His Ser Cys Asp Pro Asn
                325                 330                 335

Leu Gln Val Phe Asn Val Phe Ile Asp Asn Leu Asp Thr Arg Leu Pro
            340                 345                 350

Arg Ile Ala Leu Phe Ser Thr Arg Thr Ile Asn Ala Gly Glu Glu Leu
        355                 360                 365

Thr Phe Asp Tyr Gln Met Lys Gly Ser Gly Asp Ile Ser Ser Asp Ser
    370                 375                 380

Val Asp His Ser Pro Ala Lys Lys Arg Val Arg Thr Val Cys Lys Cys
385                 390                 395                 400

Gly Ala Val Thr Cys Arg Gly Tyr Leu Asn
                405                 410

<210> SEQ ID NO 2
<211> LENGTH: 1001
<212> TYPE: DNA
<213> ORGANISM: Canis lupus familiaris

<400> SEQUENCE: 2
tcctctatat gaagagaaaa ccttacaaag ttttgaaaag attagatgaa atacataaaa      60
tctcttgcaa aatgcctggt atttggtagt cacctcaatg aatttttctaa atacagcaat    120 aataccacaa cctaactgaa gagttctttg tattaaaatg ctttggaaaa aaaaaaaaa     180 tgctttggaa ggacgcctgg gtgctcagcg gttgagcatc ttgccttccg ctcagggcat    240
gatcccagag ttccaggatc gaatcccaca tcgggctccc tgcatggagc ctgctttttcc   300 ctctgtctgt gtcactgcac ccccccccc catctctcat gaataaacaa aatcttaaaa    360
aaaatgcttt ggaaatatta aagggtaag taacttaaat actcctcaac tatggacaaa    420
tcgttaaaaa cagtactaag ttgattagtc ctgtctattc tttaagtatc acttacactg   480
tgattaacaa aatgagagac atttccatat cgggctgcat ccactgtgaa ttcatcagat    540
tcataatcca gatcaaagag atatgtgatt cccttgttgt catataattg tccccgtctt   600
```

```
tcagcttctt cgcttgtgat tacctaaaaa gaagaaacta tagtatatta tatagctatt    660
gttgaattga acactcaccc ataaatctat tattaattta ttaatgcctt aacaacaaag    720
gtttagaaag taagaaattg aggtgtcttt aaaacaaata ttcagggatg cctgggtggt    780
tcagatggtt gggcatccac ctttggctca agtcatgatc tctagatcct gggatagagc    840
cccatgttgg ggtcccagct cagttgggag tctgcttctc cctctgtctc tcttcctgct    900
tgtgcgcgct ctctctcttg ctttcaaatg aataaaaaaa atgttaaaaa aaataaaaca    960
tatttacaca agagctacaa gagctctcta caagagctga a                       1001
```

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3

```
ctcctcaact atggacaaat cg                                             22
```

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4

```
tgccacatct ttccattcag                                                20
```

<210> SEQ ID NO 5
<211> LENGTH: 410
<212> TYPE: PRT
<213> ORGANISM: Canis lupus familiaris

<400> SEQUENCE: 5

```
Met Ala Ala Gly Ala Glu Ala Arg Arg Ala Trp Cys Val Pro Cys
1               5                  10                  15

Leu Val Ser Leu Asp Thr Leu Gln Glu Leu Cys Arg Lys Glu Lys Leu
                20                  25                  30

Thr Cys Lys Ser Ile Gly Ile Thr Lys Arg Asn Leu Asn Asn Tyr Glu
            35                  40                  45

Val Glu Tyr Leu Cys Asp Tyr Lys Val Val Lys Asp Met Glu Tyr Tyr
        50                  55                  60

Leu Val Lys Trp Lys Gly Trp Pro Asp Ser Thr Asn Thr Trp Glu Pro
65                  70                  75                  80

Leu Gln Asn Leu Lys Cys Pro Leu Leu Leu Gln Gln Phe Ser Asn Asp
                85                  90                  95

Lys His Asn Tyr Leu Ser Gln Val Lys Lys Gly Lys Ala Ile Ser Leu
            100                 105                 110

Lys Asp Asn Asn Lys Ala Leu Lys Pro Ala Ile Ala Glu Tyr Ile Val
        115                 120                 125

Lys Lys Ala Lys Gln Arg Ile Ala Leu Gln Arg Trp Gln Asp Glu Leu
    130                 135                 140

Asn Arg Arg Lys Asn His Lys Gly Met Ile Phe Val Glu Asn Thr Val
145                 150                 155                 160

Asp Leu Glu Gly Pro Pro Ser Asp Phe Tyr Tyr Ile Asn Glu Tyr Lys
                165                 170                 175
```

```
Pro Ala Pro Gly Ile Ser Leu Val Asn Glu Ala Thr Phe Gly Cys Ser
            180                 185                 190

Cys Thr Asp Cys Phe Phe Glu Lys Cys Cys Pro Ala Glu Ala Gly Val
        195                 200                 205

Leu Leu Ala Tyr Asn Lys Asn Gln Gln Ile Lys Ile Pro Pro Gly Thr
    210                 215                 220

Pro Ile Tyr Glu Cys Asn Ser Arg Cys Gln Cys Gly Pro Asp Cys Pro
225                 230                 235                 240

Asn Arg Ile Val Gln Lys Gly Thr Gln Tyr Ser Leu Cys Ile Phe Arg
                245                 250                 255

Thr Ser Asn Gly Cys Gly Trp Gly Val Lys Thr Leu Val Lys Ile Lys
            260                 265                 270

Arg Met Ser Phe Val Met Glu Tyr Val Gly Glu Val Ile Thr Ser Glu
        275                 280                 285

Glu Ala Glu Arg Arg Gly Gln Leu Tyr Asp Asn Lys Gly Ile Thr Tyr
    290                 295                 300

Leu Phe Asp Leu Asp Tyr Glu Ser Asp Glu Phe Thr Val Asp Ala Ala
305                 310                 315                 320

Arg Tyr Gly Lys Val Ser His Phe Val Asn His Ser Cys Asp Pro Asn
                325                 330                 335

Leu Gln Val Phe Asn Val Phe Ile Asp Asn Leu Asp Thr Arg Leu Pro
            340                 345                 350

Arg Ile Ala Leu Phe Ser Thr Arg Thr Ile Asn Ala Gly Glu Glu Leu
        355                 360                 365

Thr Phe Asp Tyr Gln Met Lys Gly Ser Gly Asp Ile Ser Ser Asp Ser
    370                 375                 380

Val Asp His Ser Pro Ala Lys Lys Arg Val Arg Thr Val Cys Lys Cys
385                 390                 395                 400

Gly Ala Val Thr Cys Arg Gly Tyr Leu Asn
                405                 410

<210> SEQ ID NO 6
<211> LENGTH: 1001
<212> TYPE: DNA
<213> ORGANISM: Canis lupus familiaris

<400> SEQUENCE: 6
tcctctatat gaagagaaaa ccttacaaag ttttgaaaag attagatgaa atacataaaa      60
tctcttgcaa aatgcctggt atttggtagt cacctcaatg aatttctaa atacagcaat     120 aataccacaa cctaactgaa gagttctttg tattaaaatg ctttggaaaa aaaaaaaaaa     180
tgctttggaa ggacgcctgg gtgctcagcg gttgagcatc ttgccttccg ctcagggcat     240
gatcccagag ttccaggatc gaatcccaca tcgggctccc tgcatggagc ctgcttttcc     300
ctctgtctgt gtcactgcac cccccccccc catctctcat gaataaacaa aatcttaaaa     360
aaaatgcttt ggaaatatta aagggtaag taacttaaat actcctcaac tatggacaaa     420
tcgttaaaaa cagtactaag ttgattagtc ctgtctattc tttaagtatc acttacactg     480
tgattaacaa aatgagagac ctttccatat cgggctgcat ccactgtgaa ttcatcagat     540
tcataatcca gatcaaagag atatgtgatt cccttgttgt catataattg tccccgtctt     600
tcagcttctt cgcttgtgat tacctaaaaa gaagaaacta tagtatatta tatagctatt     660
gttgaattga acactcaccc ataaatctat tattaatta ttaatgcctt aacaacaaag     720
gtttagaaag taagaaattg aggtgtcttt aaaacaaata ttcagggatg cctgggtggt     780
```

-continued

```
tcagatggtt gggcatccac ctttggctca agtcatgatc tctagatcct gggatagagc      840
cccatgttgg ggtcccagct cagttgggag tctgcttctc cctctgtctc tcttcctgct      900
tgtgcgcgct ctctctcttg ctttcaaatg aataaaaaaa atgttaaaaa aaataaaaca      960
tatttacaca agagctacaa gagctctcta caagagctga a                         1001
```

METHOD OF DETERMINING THE GENOTYPE RELATING TO HEREDITARY NASAL PARAKERATOSIS (HNPK) AND NUCLEIC ACIDS USABLE IN SAID METHOD

CROSS-REFERENCE TO RELATED APPLICATIONS

This application claims priority under 35 U.S.C. §119(a) to Finnish patent application No. 2012/5554 filed on May 25, 2012, which is incorporated by reference herein in its entirety.

FIELD OF THE INVENTION

This invention relates to an in vitro method of diagnosing a genotype relating to hereditary nasal parakeratosis (HNPK) in a dog and materials usable in said method. Particularly this invention relates to genetic variation relating to HNPK in Labrador Retrievers.

BACKGROUND

Hereditary nasal parakeratosis (HNPK) is a genodermatosis of Labrador Retrievers with a monogenic autosomal recessive inheritance (Pagé et al. 2003, Peters et al. 2003). HNPK-affected dogs develop crusts and fissuring of the nasal planum at a young age but are otherwise healthy. Histopathological changes consist of parakeratotic hyperkeratosis and an accumulation of proteinacious fluid ("serum lakes") within the stratum corneum and the superficial stratum spinosum. HNPK currently cannot be cured, but the symptoms can be alleviated with symptomatic therapy.

Due to monogenic autosomal recessive inheritance, a method to determine the genotype of a dog is of high importance. Heterozygous dogs are not affected and can phenotypically not be distinguished from homozygous free dogs. However, heterozygous dogs carry the mutant allele ("carriers") and may transmit this disease to their offspring.

At the moment breeders can identify carrier dogs only based on phenotype information collected from earlier generations and to eliminate the identified carriers from breeding programs, thereby reducing the frequency of genetic disease in a breed. Thus, there is a long felt need in the breeding of Labrador Retrievers for a genetic test that permits the identification of also healthy carriers of HNPK. Therefore, a genetic test method that can discriminate the three genotypes "free" (=homozygous wildtype), "carrier" (=heterozygous"), and "affected" (=homozygous mutant) is highly valuable for dog breeding as well as for veterinary medicine to confirm the diagnosis of suspicious cases.

SUMMARY OF THE INVENTION

An object of this invention is to provide means for identifying breeding dogs, particularly Labrador Retrievers, that are at risk of transmitting HNPK genotype to its progeny.

These and other objects are achieved by the present invention as described and claimed below.

The first aspect of the invention is an in vitro method for determining the genotype relating to hereditary nasal parakeratosis (HNPK) in a dog, comprising determining the presence or the absence of a genetic variation in the SUV39H2 gene sequence in a biological sample from said dog, and indicating that said dog suffers or will suffer from said disorder or is at risk of transmitting said disorder to its progeny if said genetic variation is present in said biological sample.

The second aspect of the invention is a polynucleotide. According to the invention the sequence of said polynucleotide is selected from the group consisting of:
a) SEQ ID NO:6,
b) a sequence being at least 80% identical to the sequence SEQ ID NO: 2, wherein said polynucleotide comprises replacement of nucleotide T with G at position 972;
c) a sequence encoding a polypeptide having SEQ ID NO: 1, wherein said polynucleotide comprises replacement of nucleotide T with G at position 972 of SUV39H2 gene;
d) a sequence encoding a polypeptide having at least 80% identity to SEQ ID NO: 1, wherein said polynucleotide comprises replacement of nucleotide T with G at position 972 of SUV39H2 gene; and
e) a sequence co complementary to any of the sequences of items (a) to (d).

The third aspect of the invention is primer pair suitable for detecting a genotype relating to hereditary nasal parakeratosis (HNPK) in a dog, comprising a first and a second primer, each comprising a contiguous span of at least 14 nucleotides of the sequence SEQ ID NO: 2 or a sequence complementary thereto, wherein:
a) said first primer hybridizes to a first DNA strand of the SUV39H2 gene;
b) said second primer hybridizes to the strand complementary to said first DNA strand of the SUV39H2 gene; and
c) the 3' ends of said first and second primers are located on regions flanking the position 972 of SEQ ID NO: 2, or of nucleotide positions complementary thereto.

The fourth aspect of the invention is a method for identifying a dog that carries a heterozygous or homozygous mutation relating to hereditary nasal parakeratosis (HNPK), comprising determining genetic variation in the SUV39H2 gene in the dog.

The fifth aspect of the invention is a method for diagnosing genotype relating to hereditary nasal parakeratosis (HNPK), comprising hybridizing a nucleic acid from a dog with an isolated nucleic acid encoding a polypeptide comprising the amino acid sequence of SEQ ID NO: 1 or an amino acid sequence at least 80% identical to said sequence, wherein nucleotide T at position 972 of the encoding gene has been replaced with G.

The sixth aspect of the invention is an in vitro method of determining the risk of hereditary nasal parakeratosis (HNPK) in a dog or its progeny, comprising determining the presence or the absence of an epitope comprising an N324K mutation in a polypeptide EC 2.1.1.43 in a biological sample from said dog, wherein the presence of said epitope indicates that said dog suffers or will suffer from said disorder or is at risk of transmitting said disorder to its progeny.

The seventh aspect of the invention is an antibody specifically recognizing the N324K epitope of dog EC 2.1.1.43 polypeptide.

BRIEF DESCRIPTION OF THE DRAWINGS

FIG. 2. Sequence context of the causative mutation for HNPK. (A) In the upper half, the sequence is shown in the same orientation as the SUV39H2 gene. (B) This gene is in minus orientation on chromosome 2. Therefore, in the lower half of the figure the flanking sequence is also shown in the forward orientation, which corresponds to the coordinates of the CanFam 3 genome assembly.

FIG. 3. Schematic presentation of the resequencing strategy of an affected Labrador retriever. A 200 bp fragment library was prepared and 3 lanes of 2×100 bp sequences were collected on an illumina HiSeq2000 instrument.; In total 1 billion reads or 100 Gb raw data corresponding to 38.5 genome coverage were collected. The flow chart shows the data analysis strategy and illustrates how the experimental sequence reads were used to determine the variants between the affected Labrador Retriever and the Boxer reference genome.

FIG. 5. Sequence conservation of the SUV39H2 protein. The figure shows an amino acid alignment in the region of the critical N324K variant, which forms part of the catalytically active SET domain. The sequence of the orthologous SUV39H2 proteins from all vertebrates is identical in the region of the N-324 residue (upper part of the alignment). Even more distantly related paralogous H3K9 methyltransferases share an asparagine residue at this position (lower part of the alignment). The high sequence conservation supports the hypothesis that a mutation of asparagine at position 324 will affect the function of the SUV39H2 protein.

FIG. 6 shows 27 annotated human genes located at region corresponding to 15 annotated genes in Labrador Retriever analyzed within this study.

DETAILED DESCRIPTION

Figure 1:
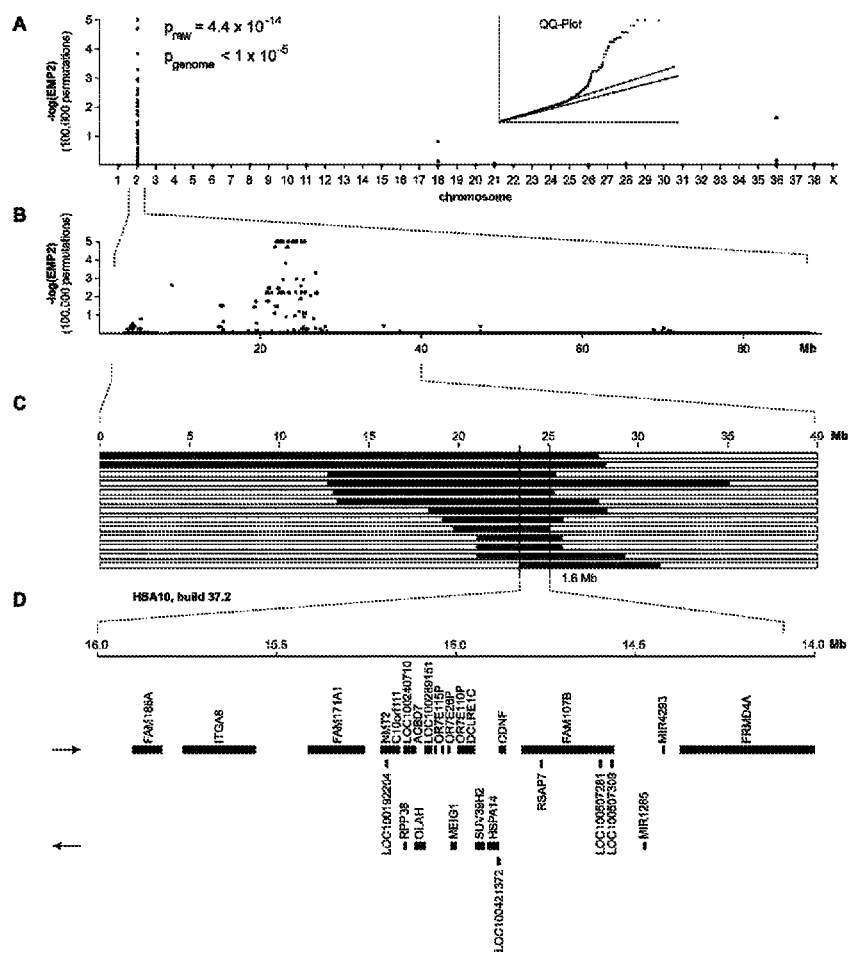
FIG. 1. Genome-wide association analysis (the coordinates in the figure refer to the previous CanFam 2.1 assembly and are not identical with the CanFam 3.1 coordinates in the text). (A) We identified a single, highly significant signal on chromosome 2. (B) The association signal was located in the first third of chromosome 2. (C) The black bars indicate homozygous segments in the 14 affected dogs. Homozygosity mapping defined an exact interval for the localization of the causative mutation. (D) Gene content of the critical interval as inferred from the corresponding human gene annotation.
Figure 4:
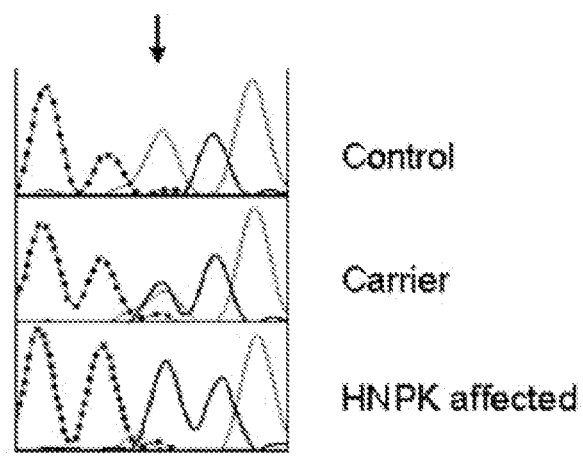
FIG. 4. SUV39H2 gene, graph showing sequencing of "Control" (healthy), "carrier" and "HNPK affected"

The invention is based on the surprising finding that genetic variation in SUV39H2 gene is related to hereditary nasal parakeratosis (HNPK) in a dog. The presence of said genetic variation indicates that said dog suffers or will suffer from said disorder or is at risk of transmitting said disorder to its progeny. This invention relates to an in vitro method of determining the genotype relating to hereditary nasal parakeratosis (HNPK) in a dog. The dog is preferably Labrador Retriever.

The SUV39H2 gene encodes a histone methylase, which specifically methylates the lysine-9 residue of histone 3 (H3K9 methylase). Trimethylation of H3K9 is a hallmark of transcriptionally silenced heterochromatin. Cells may use this epigenetic modification to turn off specific genes, whose products are no longer needed, e.g. during cell differentiation. A lack of functionally active SUV39H2 may thus lead to delayed cell differentiation. The HNPK phenotype involves hyperproliferative keratinocytes that escape their normal differentiation as they move upwards from the basal membrane to the stratum corneum of the epidermis. SUV39H2 gene is highly conserved within vertebrates.

Specifically, said genetic variation comprises a replacement of nucleotide T with G at position 972 of a gene encoding a polypeptide having SEQ ID NO: 1 or a polypeptide sequence at least 80%; preferably at least 85%, more preferably at least 90%, still more preferably at least 95% and most preferably at least 98% identical to said sequence. Said gene encoding the polypeptide having SEQ ID NO: 1 is SUV39H2 gene or a respective gene and shown as SEQ ID NO: 2.

As used in the present context the term "identity" refers to the global identity between two sequences compared to each other from the first amino acid encoded by the corresponding gene to the last amino acid. The identity of the full-length sequences is measured by using Needleman-Wunsch global alignment program. The man skilled in the art is aware of the fact that results using Needleman-Wunsch algorithm are comparative only when aligning corresponding domains of the sequence.

The presence of said genetic variation in both alleles of said SUV39H2 gene indicates that said dog suffers or will suffer from HNPK, see Table 1.

The presence of said genetic variation in one of the two alleles of said SUV39H2 gene indicates that said dog is a healthy carrier of HNPK.

The absence of said genetic variation indicates that said dog is a healthy non-carrier of HNPK.

Before this invention it has not been possible to identify healthy carriers (heterozygous) before breeding; only dogs having the variation in both genes (both alleles of the SUV39H2 gene or respective gene) have been recognized based on phenotype. It is important to avoid accidental matings of healthy carriers as offspring from such matings bear a 25% risk of being HNPK affected. According to the animal welfare legislation in many countries, it is forbidden to breed animals, if one has to expect offspring that suffers from hereditary diseases. HNPK is a hereditary disease within this part of the animal welfare legislation. Therefore, breeders are obliged by law to avoid the mating of healthy HNPK carriers.

There are numerous ways to accurately determine the SUV39H2:c.972T>G genotype of a dog. The variation can be detected using e.g. PCR, real-time PCR, melting point analysis of double-stranded DNA, mass spectroscopy, direct DNA sequencing, restriction fragment length polymorphism (RFLP), single strand conformation polymorphism (SSCP), high performance liquid chromatography (HPLC), single base primer extension, or other related methods. The critical information is that this variant really is the causative variant for the HNPK phenotype and that there is a 100% perfect correlation of the genotype at this variant with the HNPK phenotype (not considering any other hypothetical independent HNPK mutations).

The varied polynucleotide is selected from the group consisting of:
a) a sequence having SEQ ID NO: 2, wherein said polynucleotide comprises replacement of nucleotide T with G at position 972; and
b) a sequence being at least 80%, preferably at least 85%, more preferably at least 90%, still more preferably at least 95% and most preferably at least 98% identical to the sequence SEQ ID NO: 2, wherein said polynucleotide comprises replacement of nucleotide T with G at position 972; and
c) a sequence encoding a polypeptide having SEQ ID NO: 1, wherein said polynucleotide comprises replacement of nucleotide T with G at position 972 of SUV39H2 gene; and
d) a sequence encoding a polypeptide having at least 80%, preferably at least 85%, more preferably at least 90%, still more preferably at least 95% and most preferably at least 98% identity to SEQ ID NO: 1, wherein said polynucleotide comprises replacement of nucleotide T with G at position 972 of SUV39H2 gene; and
e) a sequence complementary to any of the sequences of items (a) to (d).

This invention is also directed to a pair of primers, comprising a first and a second primer and being suitable for detecting a genotype relating to hereditary nasal parakeratosis (HNPK) in a dog. Each primer comprises a contiguous span of at least 14 nucleotides of a sequence of SEQ ID NO: 2 or a sequence complementary thereto, wherein:
a) said first primer hybridizes to a first DNA strand of the SUV39H2 gene;
b) said second primer hybridizes to the strand complementary to said first DNA strand of the SUV39H2 gene; and c) the 3' ends of said first and second primers are located on regions flanking the position 972 of SEQ ID NO: 2, or of nucleotide positions complementary thereto.

Skilled man is able to adapt a suitable pair to possible slight variations within sequences of other breeds than Labrador Retriever used as an example in this study. In preferred embodiment the primers comprise at least 16, preferably 18 and most preferably at least 20 nucleotides.

In one embodiment the pair of primers have a sequence of 5'-CTCCTCAACTATGGACAAATCG-3' (SEQ ID NO: 3) and a sequence of 5'-TGCCACATCTTTCCATTCAG-3' (SEQ ID NO: 4).

A use of genetic variation in the SUV39H2 gene in a dog, preferably Labrador Retriever, as a marker for identifying a dog which carries heterozygous or homozygous mutation relating to nasal parakeratosis is within this invention.

Also a use of an oligonucleotide encoding a polypeptide having SEQ ID NO: 1 or a sequence at least 80%, preferably at least 85%, more preferably at least 90%, still more preferably at least 95% and most preferably at least 98% identical to said sequence wherein nucleotide T at position 972 of the encoding gene has been replaced with G in diagnosing genotype relating to HNPK is within the scope of this invention. Typically the encoding gene is SUV39H2 gene show as SEQ ID NO: 2.

The hereditary nasal parakeratosis (HNPK) in a dog, preferably Labrador Retriever, can also be determined in vitro based on presence or the absence of mutation in a polypeptide EC 2.1.1.43 typically being encoded by SUV39H2 gene (or respective) in a biological sample from said dog. The specific mutation at polypeptide level is N324K. The presence of said epitope indicates that said dog suffers or will suffer from said disorder or is at risk of transmitting said disorder to its progeny. Preferably the polypeptide is defined by having sequence of SEQ D NO: 1.

One of ordinary skill in the art is aware that the detection of the mutation is not restricted to any particular method, e.g. in mass spectroscopy, defining the polypeptide sequence or detection using antibodies. The antibody should specifically recognize the epitope. Examples of such antibodies are monoclonal antibodies raised against a fragment comprising said epitope or any purified antibodies.

The invention is illustrated by the following non-limiting examples. It should be understood, however, that the embodiments given in the description above and in the examples are for illustrative purposes only, and that various changes and modifications are possible within the scope of the invention.

EXAMPLES

Example 1

Identification of the Causative Mutation

We performed a genome-wide association study using 13 HNPK affected Labrador Retrievers and 23 non-affected Labrador Retriever. We genotyped these dogs at 174,376 single nucleotide polymorphisms (SNPs) evenly distributed across the genome. The analysis of the genotyping data of genome-wide association study by plink (http://pngu.mgh.harvard.edui-purcell/plink/) indicated significant differences between the cases and the controls on chromosome 2 (FIG. 2). We then further analyzed the affected dogs and found that all 13 affected dogs shared an identical homozygous segment on chromosome 2 spanning from 20,818,259-22,414,949 (CanFam 3.1 assembly). This indicates that all the HNPK affected are probably inbred to a single founder animal, which transmitted the mutant allele and spread it into the population. These results further indicate that the causative mutation for HNPK must be located in the ~1.6 Mb interval indicated above. This region at the moment contains only 15 annotated genes (NCBI MapViewer, dog genome build 3.1) shown in FIG. 2 whereas the corresponding syntenic human region contains 27 annotated genes shown in FIG. 6.

We sequenced the entire genome of an HNPK affected Labrador Retriever on an illumina HiSeq2000 instrument at 38× coverage. We compared the obtained sequenced to the Boxer reference genome and identified ~2,000 sequence variants in the critical interval of ~1.6 Mb on chromosome 2 between the HNPK affected Labrador Retriever and the Boxer reference sequence. The procedure and algorithms used are schematically illustrated in FIG. 3. Comparison resulted in the identification of 1357 SNPs and 621 indels. Among these were a total of four predicted non-synonymous variants (Table 1). One of these was an artifact due to an error in the Boxer reference sequence. The other three non-synonymous variants were tested for association with the HNPK phenotype in additional dogs (Table 1).

TABLE 1

Association of three non-synonymous variants with the HNPK phenotype

| Genotype | LA cases | LA obligate carrier | LA unrelated controls | various breeds |
|---|---|---|---|---|
| ITGA8 c.363A > G | | | | |
| A/A | 0 | 0 | 1 | 2 |
| A/G | 0 | 1 | 2 | 2 |
| G/G | 15 | 3 | 5 | 10 |
| RPP38 c.381A > G | | | | |
| A/A | 0 | 0 | 218 | 40 |
| A/G | 0 | 4 | 57 | 21 |
| G/G | 16 | 0 | 0 | 16 |
| SUV39H2 c.972T > G | | | | |
| T/T | 0 | 0 | 297 | 139 |
| T/G | 0 | 4 | 43 | 0 |
| G/G | 20 | 0 | 0 | 0 |
| NMT2 c 254delC | | error in reference sequence | | |

For one of these variants (ITGA8:c.363A>G), all three genotypes were observed in unrelated Labrador Retrievers without nose problems. Thus this variant can be excluded as being causative for HNPK. The second non-synonymous variant (RPP38:c.381A>G) showed perfect association to HNPK in a large cohort of Labrador Retrievers. However, we found the mutant allele also in many dogs from other breeds and we also found dogs from other breeds that were homozygous for the mutant allele. As HNPK is assumed to be a disease specific to the Labrador Retriever breed, we consider it highly unlikely that this variant is causative for HNPK. Finally, the third of the three non-synonymous variants, SUV39H2:c.972T>G, is perfectly associated with HNPK in a large cohort of more than 300 Labrador Retrievers. We tested also 139 healthy HNPK-free dogs from other breeds and found only the wildtype allele at this variant. Thus, the SUV39H2:c.972T>G variant seems to occur exclusively in the Labrador Retriever breed, which indicates that this variant must have arisen after the separation of modern dog breeds. This allele distribution corresponds to the scenario of a relatively young mutation event in a Labrador founder animal, which led to the spread of HNPK in this breed. Therefore, the genetic data strongly suggest that SUV39H2:c.972T>G really is the causative mutation.

On the protein level the SUV39H2:c.972T>G variant is predicted to lead to an exchange of asparagine to lysine at position 324 (p.N324K). This amino acid exchange affects an evolutionarily highly conserved position of the catalytically active so-called SET-domain of the SUV39H2 protein. In silico tools such as Sift and Polyphen strongly predict a functionally damaging effect of this variant.

In conclusion, the SUV39H2:c.972T>G variant leads to a loss of function of SUV39H2. A loss of function of SUV39H2 is expected to lead to changes in epigenetic silencing of chromatin and thus to cell differentiation defects. Thus, from a functional point of view it is plausible that SUV39H2: c.972T>G really causes HNPK.

List of Sequences:
  SEQ ID NO: 1 wild type protein encoded by SUV39H2
  SEQ ID NO: 2 wild type genomic SUV39H2 DNA
  SEQ ID NO: 3 and 4; primers
  SEQ ID NO: 5 mutated protein encoded by SUV39H2
  SEQ ID NO: 6 mutated genomic SUV39H2 DNA Application of these Findings The gained knowledge can now be used to determine the HNPK genotype of a dog. This is illustrated in Table 2.

TABLE 2

Interpretation of SUV39H2:c.972T > G genotypes

| Genotype SUV39H2 c.972T > G | Genotype HNPK |
|---|---|
| T/T | free = homozygous wildtype |
| T/G | carrier = heterozygous |
| G/G | affected = homozygous mutant |

Technical Process of Determining the SUV39H2:c.972T>G Genotype

In our lab, we PCR amplified a fragment containing exon 4 and some flanking sequences of the SUV39H2 gene using a forward primer 5'-CTCCTCAACTATGGACAAATCG-3' and a reverse primer 5'-TGCCACATCTTTCCATTCAG-3'. We subsequently sequenced the resulting ~615 bp product using Sanger sequencing technology to determine the genotype at the SUV39H2:c.972T>G variant. The details of the flanking sequence are depicted in FIG. 2.

REFERENCES

Pagé N, Paradis M, Lapointe J M, Dunstan R W: Hereditary nasal parakeratosis in Labrador Retrievers.; Vet Dermatol. 2003 April; 14(2):103-110.

Peters J, Scott D W, Erb H N, Miller W H.: Hereditary nasal parakeratosis in Labrador retrievers: 11 new cases and a retrospective study on the presence of accumulations of serum ('serum lakes') in the epidermis of parakeratotic dermatoses and inflamed nasal plane of dogs., Vet Dermatol. 2003 August; 14(4):197-203.

PLINK (1.07), http://pngu.mgh.harvard.edu/purcell/plink/

Purcell S, Neale B, Todd-Brown K, Thomas L, Ferreira M A R, Bender D, Mailer J, Sklar P, de Bakker P I W, Daly M J & Sham P C (2007) PLINK: a toolset for whole-genome association and population-based linkage analysis. American Journal of Human Genetics, 81.

The invention claimed is:

1. An in vitro method for genotyping a Labrador Retriever comprising:
   a) obtaining a biological sample from the Labrador Retriever;
   b) genotyping a SUV39H2 gene encoding the polypeptide of SEQ ID NO: 1 and
   c) detecting the presence of a replacement of a nucleotide T with a nucleotide G at position 972 of SEQ ID NO: 2.

2. The method according to claim 1, wherein the genotyping is achieved by PCR, real-time PCR, melting point analysis of double-stranded DNA, mass spectroscopy, direct DNA sequencing, restriction fragment length polymorphism (RFLP), single strand conformation polymorphism (SSCP), high performance liquid chromatography (HPLC), or single base primer extension.

3. The method of claim 1, wherein the genotyping utilizes a primer pair comprising a first primer and a second primer, each comprising a contiguous span of at least 14 nucleotides of the sequence SEQ ID NO: 2 or a sequence complementary thereto, wherein:
   a) said first primer hybridizes to a first DNA strand of the SUV39H2 gene;
   b) said second primer hybridizes to the strand complementary to said first DNA strand of the SUV39H2 gene; and
   c) the 3' ends of said first and second primers are located on regions flanking the position 972 of SEQ ID NO: 2, or of nucleotide positions complementary thereto.

4. The method of claim 3, wherein the first primer comprises the sequence of 5'-CTCCTCAACTATGGACAAATCG-3' (SEQ ID NO: 3) and the second primer comprises the sequence of 5'-TGCCACATCTTTCCATTCAG-3' (SEQ ID NO: 4).

5. An in vitro method for genotyping a Labrador Retriever comprising:
   a) obtaining a biological sample from the Labrador Retriever;
   b) contacting the nucleic acid from the biological sample with an isolated nucleic acid encoding a polypeptide comprising the amino acid sequence of SEQ ID NO: 1, wherein the nucleotide T at position 972 of SEQ ID NO: 2 has been replaced with G and
   c) detecting the presence of a hybridized nucleic acid encoding a polypeptide comprising the amino acid sequence of SEQ ID NO: 1, wherein the nucleotide T at position 972 of SEQ ID NO: 2 has been replaced with G.

* * * * *